United States Patent
Abedin et al.

(10) Patent No.: US 10,556,053 B2
(45) Date of Patent: Feb. 11, 2020

(54) SYSTEM FOR COLLECTING MONONUCLEAR CELLS HAVING A SUITABLE HEMATOCRIT FOR EXTRACORPOREAL PHOTOPHERESIS

(71) Applicant: Fenwal, Inc., Lake Zurich, IL (US)

(72) Inventors: Tanima Jahan Abedin, Chicago, IL (US); Katherine N. Radwanski, Highland Park, IL (US)

(73) Assignee: Fenwal, Inc., Lake Zurich, IL (US)

( * ) Notice: Subject to any disclaimer, the term of this patent is extended or adjusted under 35 U.S.C. 154(b) by 83 days.

(21) Appl. No.: 15/881,806

(22) Filed: Jan. 29, 2018

(65) Prior Publication Data

US 2018/0214626 A1    Aug. 2, 2018

Related U.S. Application Data

(60) Provisional application No. 62/452,039, filed on Jan. 30, 2017.

(51) Int. Cl.
*A61M 1/00*    (2006.01)
*A61M 1/36*    (2006.01)
(Continued)

(52) U.S. Cl.
CPC ........ *A61M 1/3609* (2014.02); *A61M 1/3681* (2013.01); *A61M 1/3683* (2014.02);
(Continued)

(58) Field of Classification Search
USPC ....... 210/32, 285, 86, 97, 143, 380.1, 512.1, 210/739, 744, 781, 782, 787, 789; 356/218, 246; 422/22, 72; 494/1, 37, 10, 494/16, 18, 21, 38, 41, 43, 45, 84
See application file for complete search history.

(56) References Cited

U.S. PATENT DOCUMENTS

| 5,360,542 A | 11/1994 | Williamson, IV et al. |
| 5,868,696 A | 2/1999 | Giesler et al. |

(Continued)

FOREIGN PATENT DOCUMENTS

| EP | 1754497 A1 | 2/2007 |
| EP | 2813253 A2 | 12/2014 |

(Continued)

OTHER PUBLICATIONS

Jelin, "Potential Mechanisms of Photopheresis in Hematopoietic Stem Cell Transplantation," Biology of Blood and Marrow Transplantation 12:7-12 (2006).

(Continued)

*Primary Examiner* — Hayden Brewster
(74) *Attorney, Agent, or Firm* — Cook Alex Ltd.

(57) ABSTRACT

A system for collecting MNCs to be treated with irradiation comprises a fluid circuit comprising a product container for receiving a MNC product. The system comprises a separator to work in association with the fluid circuit, the separator comprising a chamber for separation into RBCs, plasma, and an interface carrying MNCs between the RBCs and the plasma. A microprocessor-based controller is in communication with the separator, wherein the controller receives input of a target hematocrit for the MNC product. The controller also receives input for a total volume of whole blood and a number of cycles, and directs the interface and a portion of the RBCs into the product container for a resulting product volume comprising a volume of MNCs and a volume of RBCs. The controller automatically adjusts a RBC volume so that a ratio of RBCs within the MNC product to MNC product equals the target hematocrit.

6 Claims, 7 Drawing Sheets

(51) Int. Cl.
*A61M 1/38* (2006.01)
*B01D 21/26* (2006.01)
*B04B 5/04* (2006.01)
*B01D 1/00* (2006.01)

(52) U.S. Cl.
CPC .......... *A61M 1/3696* (2014.02); *A61M 1/382* (2013.01); *B01D 21/26* (2013.01); *B04B 5/0442* (2013.01); *A61M 2202/0439* (2013.01); *A61M 2205/053* (2013.01); *A61M 2230/207* (2013.01); *B01D 2221/10* (2013.01)

(56) References Cited

U.S. PATENT DOCUMENTS

| | | |
|---|---|---|
| 5,980,760 A | 11/1999 | Min et al. |
| 6,027,657 A | 2/2000 | Min et al. |
| 7,282,154 B2 | 10/2007 | Muller |
| 7,433,030 B2 | 10/2008 | Waldo et al. |
| 2015/0196706 A1 | 7/2015 | Radwanski et al. |
| 2016/0114095 A1* | 4/2016 | Radwanski ......... A61M 1/3693 424/93.71 |
| 2016/0195555 A1 | 7/2016 | Wegener et al. |

FOREIGN PATENT DOCUMENTS

| | | | |
|---|---|---|---|
| EP | 2813253 A3 | 3/2015 | |
| EP | 3015125 A1 | 5/2018 | |

OTHER PUBLICATIONS

European Search Report for application No. 118153889.3, dated Jun. 21, 2018, 10 pages.

* cited by examiner

SYSTEM FOR COLLECTING MONONUCLEAR CELLS HAVING A SUITABLE HEMATOCRIT FOR EXTRACORPOREAL PHOTOPHERESIS

CROSS-REFERENCE TO RELATED APPLICATIONS

This application claims the benefit of U.S. Provisional Patent App. No. 62/452,039 filed Jan. 30, 2017, which is expressly incorporated herein by reference in its entirety.

FIELD OF THE DISCLOSURE

The present disclosure relates generally to performing extracorporeal photopheresis of mononuclear cells and, in particular to a method of maintaining a suitable hematocrit of a mononuclear cell product to be irradiated as part of a photopheresis treatment.

BACKGROUND

Whole blood is made up of various cellular and non-cellular components such as red cells, white cells and platelets suspended in its liquid component, plasma. Whole blood may be separated into its constituent components (cellular, liquid or other), and the separated component(s) may be administered to a patient in need of that particular component or components.

The administration of blood and/or blood components is common in the treatment of patients suffering from disease. Rather than infuse whole blood, individual components may be administered to the patient(s) as their needs require. For example, administration (infusion) of platelets may often be prescribed for cancer patients whose ability to make platelets has been compromised by chemotherapy. Infusion of white blood cells (i.e., mononuclear cells) after the cells have undergone some additional processing or treatment may also be prescribed for therapeutic reasons, including treatment of diseases that specifically involve the white blood cells. Thus, it may be desirable to separate and collect the desired blood component from whole blood and then treat the patient with the specific blood component. The remaining components may be returned to the patient or retained for other uses.

There are several diseases or disorders which are believed to primarily involve mononuclear cells, such as cutaneous T-cell lymphoma, organ allograft rejection after transplantation and autoimmune diseases such as rheumatoid arthritis and systemic sclerosis, among others.

Cutaneous T-cell lymphoma (CTCL) is a term that is used to describe a wide variety of disorders. Generally, CTCL is a type of cancer of the immune system where T-cells (a type of mononuclear cell) mutate or grow in an uncontrolled way, migrate to the skin and form itchy, scaly plaques or patches. More advanced stages of the disease also affect the lymph nodes. Therapeutic treatment options for CTCL have previously been limited. While chemotherapy has been utilized, this particular form of treatment also has many associated undesirable side effects, such as lowered resistance to infection, bleeding, bruising, nausea, infertility and hair loss, just to name a few.

Organ allograft rejection may be characterized as the rejection of tissues that are foreign to a host, including transplanted cardiac tissue as well as lung, liver and renal transplants. Immunosuppression drug therapy following transplantation is common. However, there are potential drawbacks including reoccurring infection due to the compromised competence of the immune system caused by this type of therapy.

Similarly, graft versus host disease (GVHD) is a complication that can occur after a stem cell or bone marrow transplant in which the newly transplanted material attacks the transplant recipient's body. The differences between the donor's cells and recipient's tissues often cause T-cells from the donor to recognize the recipient's body tissues as foreign, thereby causing the newly transplanted cells to attack the recipient. GVHD may complicate stem cell or bone marrow transplantation, thereby potentially limiting these life-saving therapies. Therefore, after a transplant, the recipient is usually administered a drug that suppresses the immune system, which helps reduce the chances or severity of GVHD.

Autoimmune diseases, including rheumatoid arthritis (RA) and progressive systemic sclerosis (PSS), can be characterized by an overactive immune system which mistakes the body's own tissues as being a foreign substance. As a result, the body makes autoantibodies that attack normal cells and tissues. At the same time, regulatory T-cells, which normally function to regulate the immune system and suppress excessive reactions or autoimmunity, fail in this capacity. This may lead to among other things, joint destruction in RA and inflammation of the connective tissue in PSS.

SUMMARY

According to an exemplary embodiment, the present disclosure is directed to a method for collecting diluted mononuclear cells to be treated with UV irradiation, driven and adjusted by a microprocessor-based controller. The method comprises receiving input of a target hematocrit for a mononuclear cell product to be collected in a first container comprising mononuclear cells and red blood cells, wherein hematocrit is determined by a ratio of the red blood cells per volume within the mononuclear cell product. The method also comprises rotating a chamber about a rotational axis and conveying a volume of whole blood into an inlet region of the chamber for separation into a red blood cell constituent, a plasma constituent, and an interface carrying mononuclear cells between the red blood cell constituent and the plasma constituent. The method also comprises collecting a first volume of red blood cells in a second container, wherein the first volume of red blood cells comprises a portion of total red blood cells in the volume of whole blood, and collecting a first volume of mononuclear cells, a second volume of red blood cells, and a volume of plasma in the first container, wherein the second volume of red blood cells comprises a portion of total red blood cells in the volume of whole blood. The method also comprises transferring a third volume of red blood cells from the second container into the first container if contents of the first container has an actual hematocrit less than the target hematocrit, wherein the third volume of red blood cells in combination with the second volume of red blood cells achieves the target hematocrit for the mononuclear cell product.

According to an exemplary embodiment, the present disclosure is directed to a method for collecting diluted mononuclear cells to be treated with UV irradiation, driven and adjusted by a microprocessor-based controller, comprising receiving input of a target hematocrit for a mononuclear cell product to be collected in a first container comprising mononuclear cells, red blood cells, and plasma, wherein hematocrit is determined by a ratio of the red blood cells per volume within the mononuclear cell product. The method also comprises receiving input for a total volume of whole blood to be processed and a number of cycles to be performed, and rotating a chamber about a rotational axis and conveying whole blood into an inlet region of the chamber for separation into a red blood cell constituent, a plasma constituent, and an interface carrying mononuclear cells between the red blood cell constituent and the plasma constituent, wherein separation is performed across a plurality of cycles. The method also comprises, in a first cycle, directing the interface and a portion of the red blood cell constituent into the first container by opening a valve disposed between the chamber and the first container for a first product volume comprising a first volume of mononuclear cells and a first volume of red blood cells. The method also comprises, in a second cycle, directing the interface and red blood cell constituent into the first container by opening the valve for a second product volume comprising a second volume of mononuclear cells and a second volume of red blood cells. The microprocessor-based controller is configured to automatically adjust the first and/or second product volumes so that a volume ratio of a total volume of red blood cells within the mononuclear cell product to a total volume of mononuclear cell product equals the target hematocrit.

According to an exemplary embodiment, the present disclosure is directed to a system for collecting mononuclear cells to be treated with UV irradiation. The system comprises a disposable fluid circuit comprising a product container configured to receive a mononuclear cell product comprising mononuclear cells, red blood cells, and plasma. The system also comprises a separator configured to work in association with the disposable fluid circuit, the separator comprising a chamber configured to rotate about a rotational axis and convey whole blood into an inlet region of the chamber for separation into a red blood cell constituent, a plasma constituent, and an interface carrying mononuclear cells between the red blood cell constituent and the plasma constituent. The system also comprises a microprocessor-based controller in communication with the separator, wherein the controller is configured to receive input of a target hematocrit for the mononuclear cell product, wherein hematocrit is determined by a ratio of the red blood cells per volume within the mononuclear cell product. The controller is also configured to receive input for a total volume of whole blood to be processed and a number of cycles to be performed, and direct the interface and a portion of the red blood cell constituent into the product container by opening a valve disposed between the chamber and the product container for a resulting product volume comprising a volume of mononuclear cells and a volume of red blood cells. The controller is also configured to automatically adjust a RBC volume so that a ratio of total volume of red blood cells within the mononuclear cell product to a total volume of mononuclear cell product equals the target hematocrit.

BRIEF DESCRIPTION OF THE DRAWINGS

Features, aspects, and advantages of the present embodiments will become apparent from the following description, appended claims, and the accompanying exemplary embodiments shown in the drawings, which are briefly described below.

DETAILED DESCRIPTION

Figure 1:
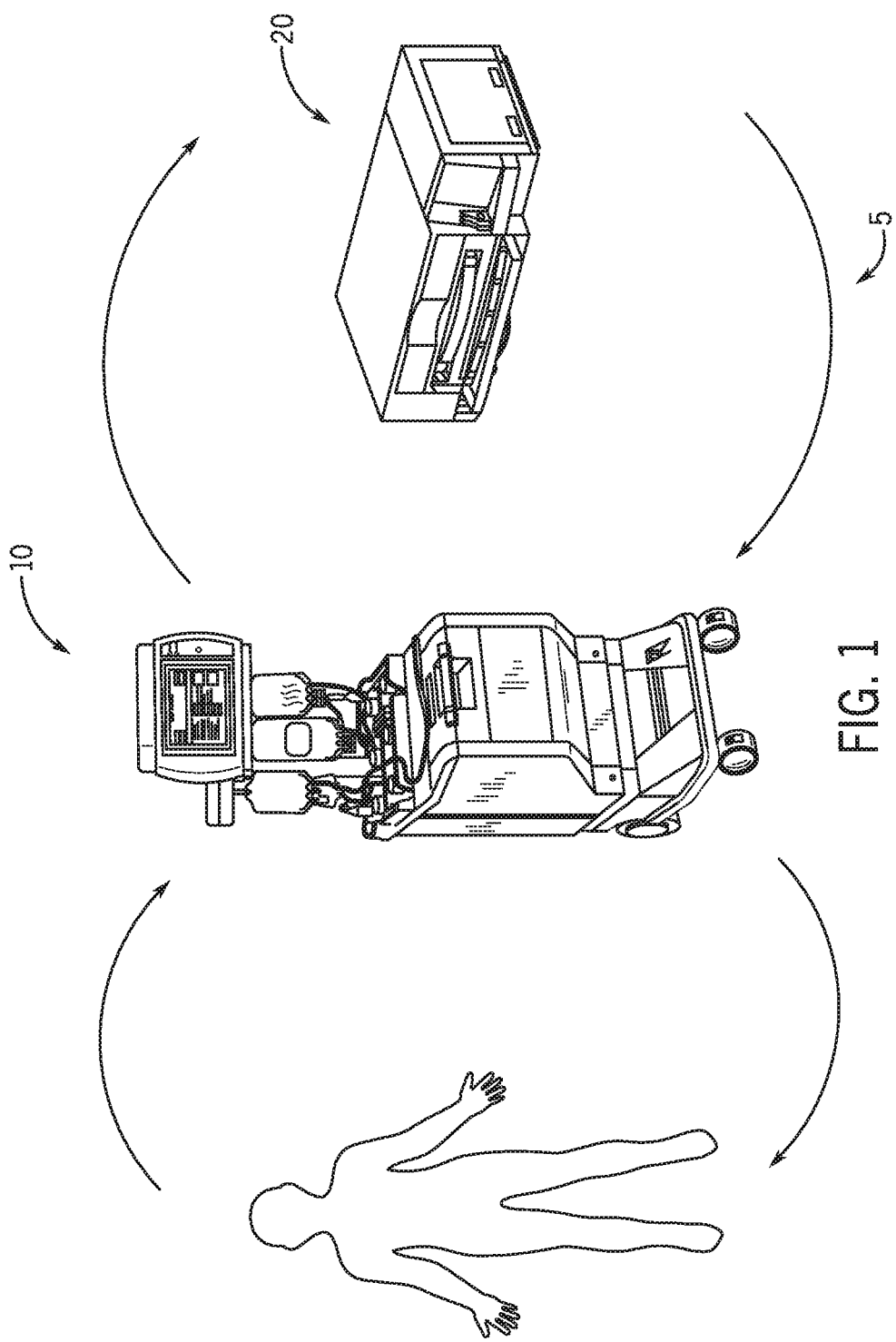
FIG. 1 is a diagram generally showing the mechanical components of a photopheresis treatment device, according to an exemplary embodiment.

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

Where existing therapies for treating one or more diseases may result in certain unintended side effects, additional treatment may be desired or required. One procedure which has been shown to be effective in the treatment of diseases and/or the side effects of existing therapies involving mononuclear cells is extracorporeal photopheresis or "ECP". Extracorporeal photopheresis (also sometimes referred to as extracorporeal photochemotherapy) is a process that includes: (1) collection of mononuclear cells (MNC) from a patient, (2) photoactivation treatment of the collected MNC cells; and (3) re-infusion of the treated cells (MNC) back to the patient. More specifically, ECP involves the extracorporeal exposure of peripheral blood mononuclear cells combined with a photoactive compound, such as 8-methoxypsoralen or "8-MOP" which is then photoactivated by ultraviolet light, followed by the re-infusion of the treated mononuclear cells. The combination of 8-MOP and UV radiation may cause apoptosis or programmed cell death of ECP-treated T-cells.

During ECP treatment, photoactivation is known to cause 8-MOP to irreversibly covalently bind to the DNA strands contained in the T-cell nucleus. When the photochemically damaged T-cells are reinfused, cytotoxic effects are induced. For example, a cytotoxic T-cell or "CD8+ cell" releases cytotoxins when exposed to infected or damaged cells or otherwise attacks cells carrying certain foreign or abnormal molecules on their surfaces. The cytotoxins target the damaged cell's membrane and enter the target cell, which eventually leads to apoptosis or programmed cell death of the targeted cell. In other words, after the treated mononuclear cells are returned to the body, the immune system recognizes the dying abnormal cells and begins to produce healthy lymphocytes (T-cells) to fight against those cells.

Extracorporeal photopheresis may also induce monocytes (a type of mononuclear cell) to differentiate into dendritic cells capable of phagocytosing and processing apoptotic T-cells. When these activated dendritic cells are re-infused into systemic circulation, they may cause a systemic cytotoxic CD8+ T-lymphocyte-mediated immune response to the processed apoptotic T-cell antigens like that described above.

ECP may result in an immune tolerant response in the patient. For example, in the case of graft versus-host disease, the infusion of apoptotic cells may stimulate regulatory T-cell generation, inhibit inflammatory cytokine production, cause the deletion of effective T-cells and result in other responses. See Peritt, "Potential Mechanisms of Photopheresis in Hematopoietic Stem Cell Transplantation," Biology of Blood and Marrow Transplantation 12:7-12 (2006). While presently the theory of an immune tolerant response appears to be among the leading explanations, there exist still other theories as to the mechanism of action of ECP relative to graft-versus-host disease, as well as other disease states.

In performing an ECP procedure for MNCs, it is desirable to deliver the proper dose of light energy to the photoactivatable material in the suspension within which the MNCs are suspended, particularly if the suspension includes material (such as red blood cells) that is not substantially transparent to light so that it attenuates the light energy intended for photoactivation. The proper dose may be determined and administered by the use of a hematocrit sensor, light sensors, and/or algorithm that utilize information regarding thickness, hematocrit, and light transmittance values of the suspension. Examples relating to determining the proper light dosage and exposure are described in US. Pat. Pub. Nos. 2015/0196706 and 2016/0195555, the contents of which are incorporated by reference herein in their entireties.

Some embodiments may allow for maintaining MNG product hematocrit at acceptable hematocrit values to optimize levels of irradiation delivered to the target cells.

Some embodiments may enable the processing of variable whole blood volumes during collection of MNCs while maintaining control of the hematocrit.

In some embodiments, over-irradiation of MNCs during an ECP procedure may be avoided, so that cells do not prematurely undergo apoptosis or necrosis prior to re-entering the patient's bloodstream, thereby minimizing compromise to the intended immune response and the therapeutic effects of the ECP procedure.

Figure 2:
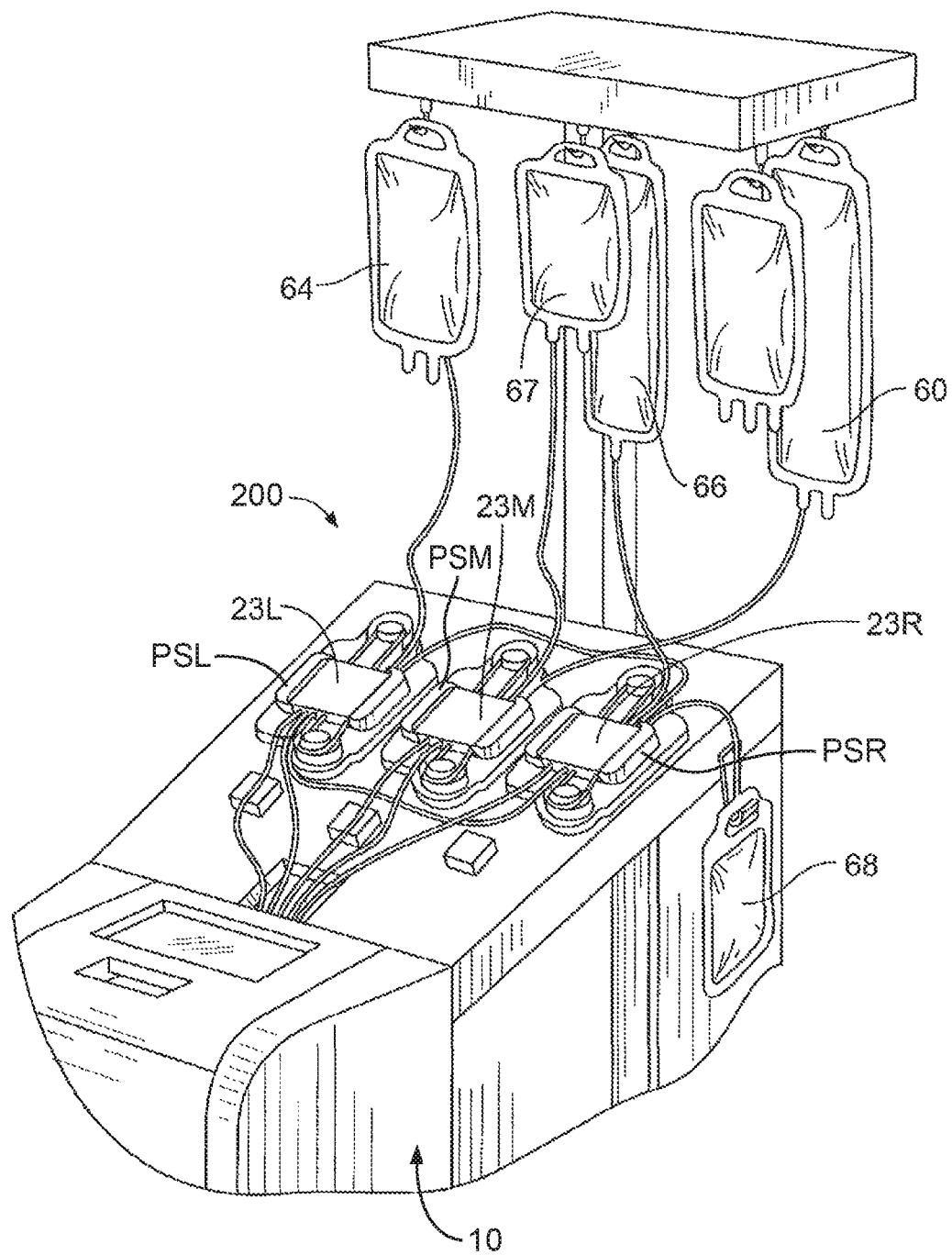
FIG. 2 is a partial perspective view of an apheresis separator useful in the methods and systems described herein, according to an exemplary embodiment.
Figure 4:
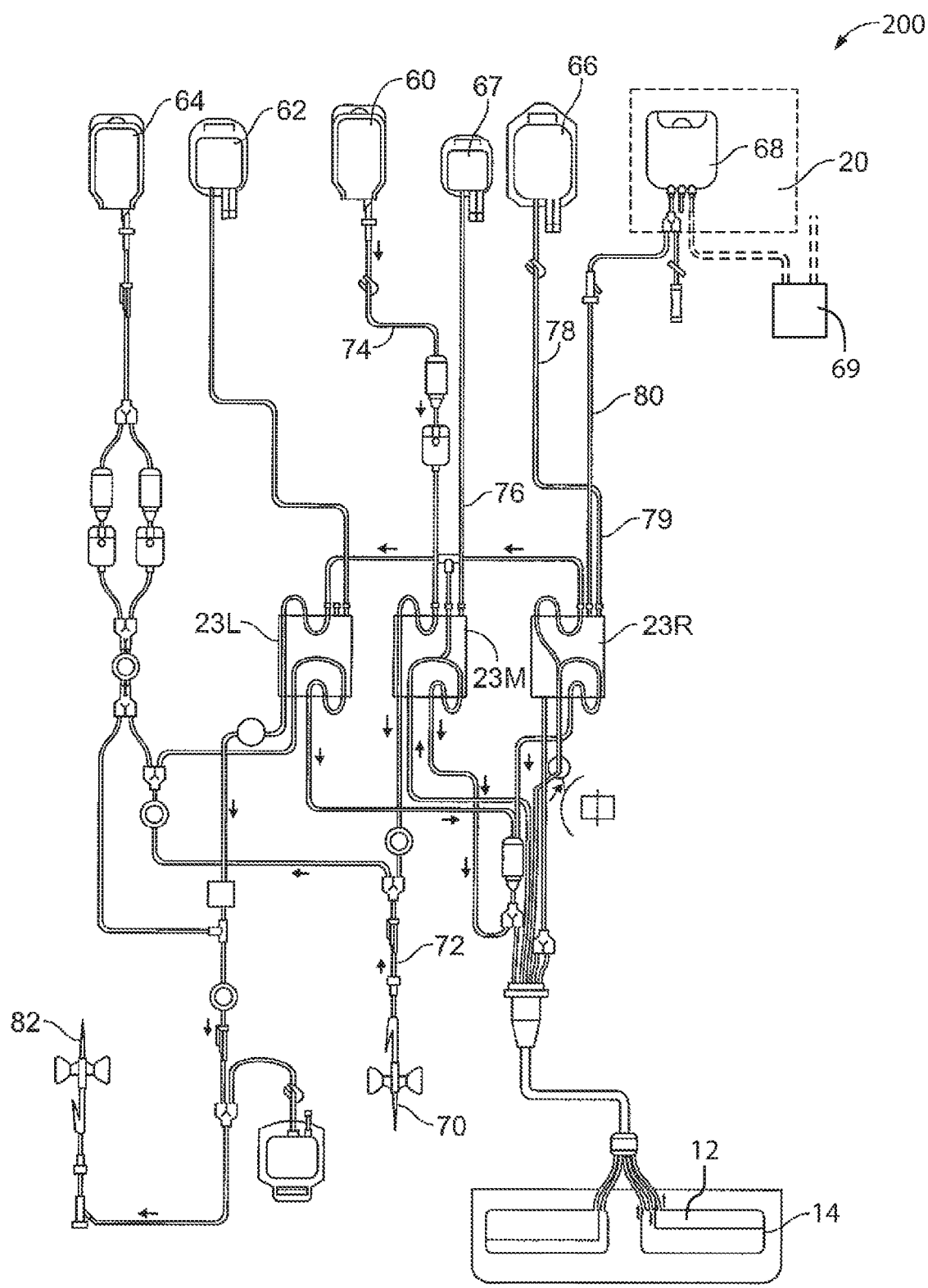
FIG. 4 is a diagram of the fluid circuit useful in the collection, treatment and reinfusion of target cells, according to an exemplary embodiment.

FIG. 1 shows, in general, the mechanical components that make up an ECP system 5 and that may be used in one or more of the systems and methods described herein. The system 5 may include a separation component 10 and a treatment (i.e., irradiation) component 20. Irradiation component 20 may be independent and housed separately from the separation component 10, or components 20 and 10 may be integrated into a single device. In an embodiment in which components 20 and 10 are housed separately, the separation device 10 and irradiation device 20 may be located adjacent to each other, allowing an operator or clinician to have access to both devices during a particular treatment procedure. A patient may be connected to a fluid circuit 200 as shown in FIGS. 1, 2, 4 that provides a sterile closed pathway between separation component 10 and irradiation component 20 and may be cooperatively mounted on the hardware of the separation device 10. The separation device 10 may have one or more features of an apheresis device, such as a system marketed as the AMICUS® separator by Fenwal, Inc. of Lake Zurich, Ill., as described in greater detail in U.S. Pat. No. 5,868,696, which is hereby incorporated herein by reference in its entirety, although any suitable separation device may be used. Although the embodiments disclosed herein are described in conjunction with a separation device 10, the present embodiments may be applicable to an irradiation device 20 alone, in which case the target cell population may be provided to the irradiation device 20 subsequent to being collected elsewhere.

With reference to FIG. 1, whole blood may be withdrawn from the patient and introduced into the separation component 10 where the whole blood is separated to provide a target cell population. In one embodiment, the target cell population may be mononuclear cells (MNCs) or MNCs of a particular type (lymphocytes, monocytes, and/or dendritic cells, etc.). Other components separated from the whole blood, such as red blood cells (RBCs), plasma, and/or platelets may be returned to the patient or collected in pre-attached containers of the blood processing set.

The separated target cell population, e.g., mononuclear cells, may then be treated and irradiated in treatment component 20. As discussed above, treatment of mononuclear cells may involve the photoactivation of a photoactive agent that has been combined with the mononuclear cells. Mononuclear cell collection, harvest, and transfer using a device such as the Amicus® are described in greater detail in U.S. Pat. No. 6,027,657, the contents of which are incorporated by reference herein in its entirety. Preferably, the apparatus used for the harvesting, collection and reinfusion of mononuclear cells may be a "multifunctional" automated apheresis device, as is the case with the Amicus® Separator. In other words, the separation component 10 may be a multifunctional automated apparatus that can perform various collection protocols and/or serve multiple purposes, as may be needed by a particular hospital or facility, such that it can be used not only in the systems and methods for performing photopheresis treatment of MNC as described herein, but can also be used for other purposes including the collection of blood and blood components including platelets, plasma, red blood cells, granulocytes and/or perform plasma/RBC exchange, among other functions required by the hospital or medical facility.

Figure 3:
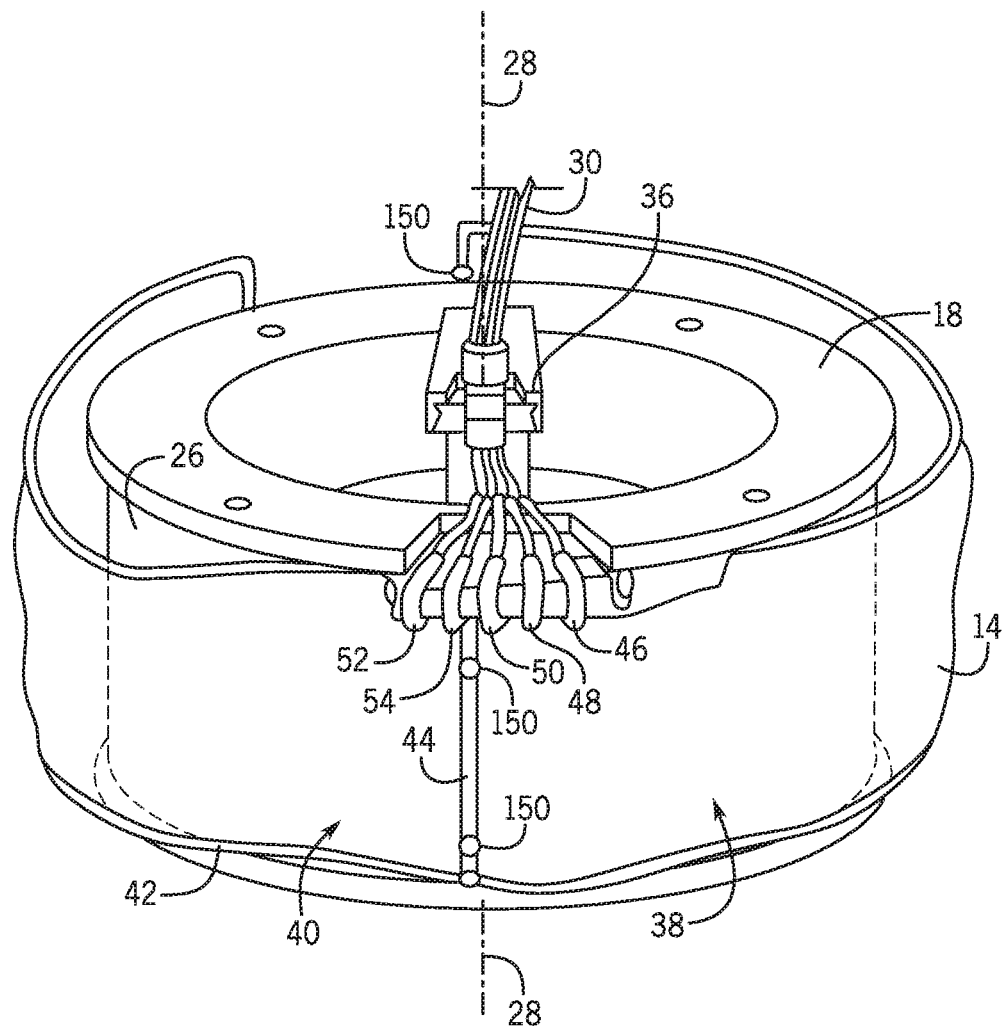
FIG. 3 is a perspective view of a separation chamber of the processing set used with the separator of FIG. 2, according to an exemplary embodiment.

FIGS. 2-4 depict a separator 10 with fluid circuit 200 mounted thereon (FIG. 2), the fluid circuit (FIG. 4) having a blood processing container 14 (FIG. 3) defining a separation chamber 12 suitable for harvesting mononuclear cells (MNC) from whole blood. As shown in FIG. 2, a disposable processing set or fluid circuit 200 (which includes container 14) may be mounted on the front panel of separator 10. The fluid circuit 200 may include a plurality of processing cassettes 23L, 23M and 23R with tubing loops for association with peristaltic pumps on separator 10. Fluid circuit 200 may also include a network of tubing and pre-connected containers for establishing flow communication with the patient and for processing and collecting fluids and blood and blood components, as shown in FIG. 4. As seen in FIGS. 2 and 4, disposable processing set 200 may include a container 60 for supplying anticoagulant, a waste container 62 for collecting waste from one or more steps in the process for treating and washing mononuclear cells, a container 64 for holding saline or other wash or resuspension medium, a container 66 for collecting plasma, a container 68 for collecting the mononuclear cells and, optionally, container 69 for holding the photoactivation agent.

Container 68 may also serve as the illumination container, and the illumination container 68 may be pre-attached to and integral with the disposable set 200. Alternatively, container 68 may be attached to set 200 by known sterile connection techniques, such as sterile docking or the like. In FIG. 2, container 68 is shown as suspended from device 10. However, container 68 may be housed within an adjacent separately housed irradiation device 20 (as shown by broken lines in FIG. 4), thereby eliminating the step of having the operator place container 68 into irradiation device 20. The tubing leading to and/or from container 68 in fluid circuit 200 may be of a sufficient length to reach an irradiation device 20 that is adjacent to but housed separately from the separation device.

With reference to FIG. 4, fluid circuit 200 may include inlet line 72, an anticoagulant (AC) line 74 for delivering AC from container 60, an RBC line 76 for conveying red blood cells from chamber 12 of container 14 to container 67, a platelet poor plasma (PPP) line 78 for conveying PPP to container 66 and line 80 for conveying mononuclear cells to and from blood processing container 14 and collection/illumination container 68. The blood processing set may include one or more venipuncture needle(s) for accessing the circulatory system of the patient. As shown in FIG. 4, fluid circuit 200 may include inlet needle 70 and return needle 82. In an alternative embodiment, a single needle may serve as both the inlet and outlet needle.

Fluid flow through fluid circuit 200 may be driven, controlled and adjusted by a microprocessor-based controller in cooperation with the valves, pumps, weight scales and sensors of device 10 and fluid circuit 200, the details of which are described in the aforementioned U.S. Pat. No. 6,027,657, although any suitable controller may be used. Fluid flow through the circuit 200 may also be discerned and visualized by an optical sensor and/or hematocrit sensor (not illustrated) part of the device 10 to sense and quantify MNCs, RBCs, and/or plasma for harvesting. Details regarding a suitable optical sensor and method of blood component visualization are also described in U.S. Pat. No. 6,027,657. Details regarding a suitable hematocrit sensor is described in U.S. Pat. No. 7,282,154, which is incorporated by reference herein in its entirety.

In accordance with the present disclosure, the fluid circuit may be further adapted for association with the irradiation device 20. One example of a suitable irradiation device is described in U.S. Pat. No. 7,433,030, which is incorporated by reference herein in its entirety, although any suitable irradiation device may be used. The irradiation device 20 may include a tray or other holder for receiving one or more containers during treatment.

Referring to FIG. 3, separation chamber 12 is defined by the walls of a flexible processing container 14 carried within an annular gap defined by a rotating spool element 18 and an outer bowl element (not shown). The blood processing container 14 may take the form of an elongated tube which is wrapped about the spool element 18 before use. The bowl and spool element 18 may be pivoted on a yoke between an upright position and a suspended position. In operation, the centrifuge 10 may rotate the suspended bowl and spool element 18 about an axis 28, creating a centrifugal field within the processing container 14. Details of the mechanism for causing relative movement of the spool 18 and bowl elements as described are disclosed in U.S. Pat. No. 5,360,542 entitled "Centrifuge with Separable Bowl and Spool Elements Providing Access to the Separation Chamber," which is also incorporated herein by reference in its entirety, although any suitable separation mechanism may be used.

Figure 5:
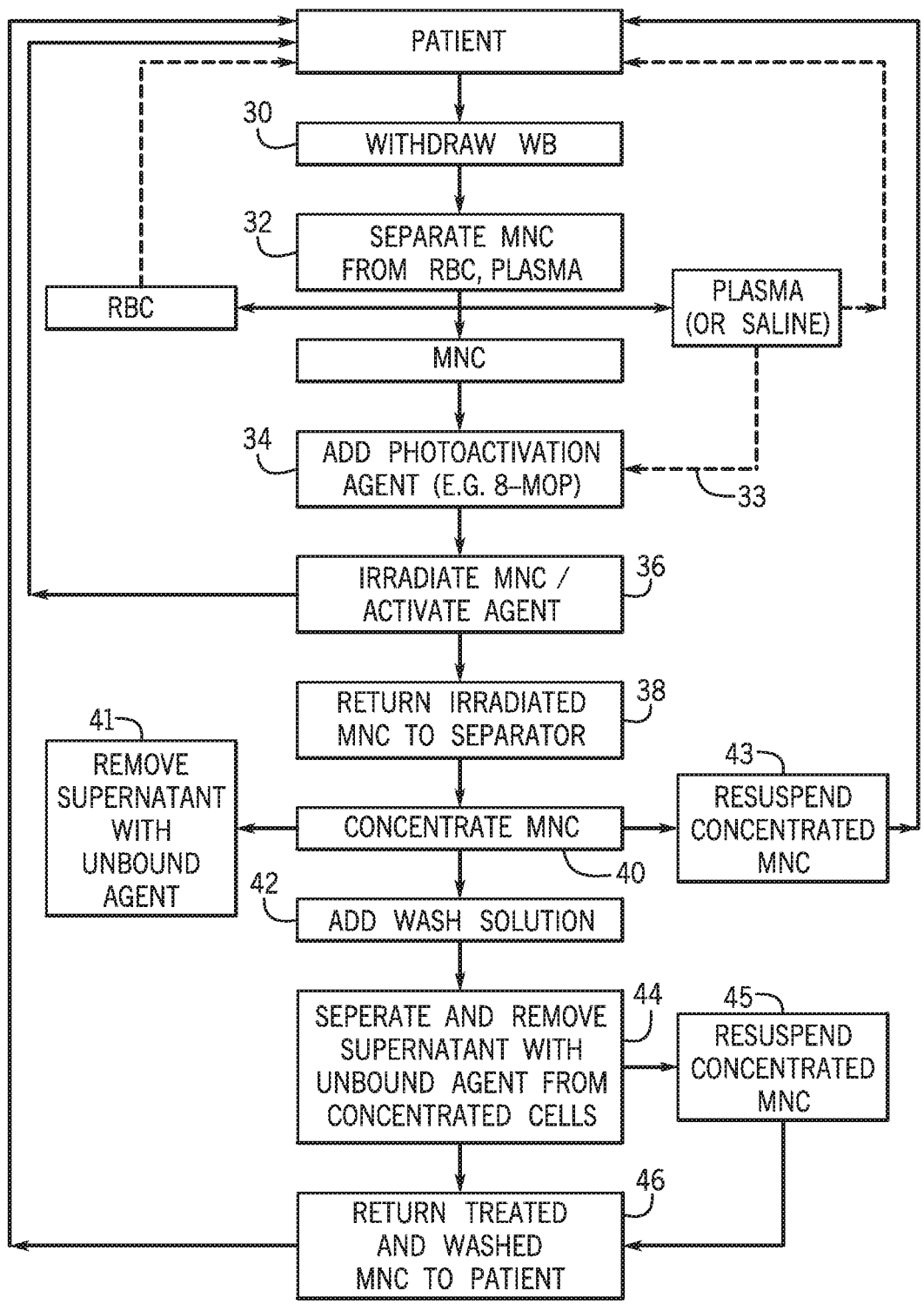
FIG. 5 is a flow chart setting forth a portion of the steps of the method of an online photopheresis treatment, according to an exemplary embodiment.

FIG. 5 depicts one embodiment of an online method of treating mononuclear cells. An "online" photopheresis system includes both the blood separation device and the irradiation device in an integrated system. An online system provides for reinfusion of treated target cells back to the patient. Whole blood may first be withdrawn from a patient (step 30) through inlet needle 70 and introduced into the separation chamber 12 of container 14 of processing set 200, where the whole blood is subjected to a centrifugal field. The centrifugal field may separate the target cell population, i.e., mononuclear cells, from a red blood cell constituent and a platelet/plasma (step 32). The components such as red blood cells and platelets may be returned to the patient or may be diverted to a container (e.g., container 67) for further processing. Collection of the mononuclear cells may proceed in one or more cycles, with the number of processing cycles conducted in a given therapeutic procedure depending upon the total yield of MNCs to be collected. Although FIG. 5 depicts an online method of treating MNCs, offline methods are available as well. In offline methods, an apheresis device may be used to collect target cells. The collected target cells, typically contained in one or more collection containers, are severed or otherwise separated from the tubing set used during collection, where they are later treated in a separate irradiation or UVA light device followed by subsequent reinfusion of the treated cells to a patient. During such offline methods, when the cells are transferred from the apheresis device to the irradiation device (which device may be located in another room or laboratory), communication with the patient is severed and the cells detached from the patient.

Effective treatment of the MNCs with light may be facilitated by collecting mononuclear cells in a suspension having a suitable hematocrit. The level of hematocrit of the MNC suspension to be treated may affect the amount of UV light absorbed by the MNCs, given that the red blood cells in the MNC suspension block at least a portion the UV light from reaching the targeted MNCs. Control of hematocrit may be desirable in cases in which the light source of the irradiation device is configured to irradiate a set intensity of light, limited settings of light intensity values, and/or a set dose of irradiation, although hematocrit control may be desirable also in cases in which intensity, dose, and/or exposure settings may readily be adjusted according to hematocrit. It is common for a transmitter (e.g., bank of light bulbs) of an irradiation device to not be adjustable in terms of intensity of emission and therefore may emit a near-constant intensity of light. If the hematocrit of the suspended MNCs is too high (such that the red blood cells prevent the absorption of light by the MNCs), it may be desired to dilute the mononuclear cells with a diluting solution, such as plasma or saline, as shown in step 33 (FIG. 5), to control the hematocrit so that a desired amount of UV light will reach the targeted MNC. The diluted mononuclear cells (in container 68) may then be combined with the suitable photoactivation agent in step 34. On the other hand, if the hematocrit of the suspended MNCs is too low, the RBCs may not provide adequate blockage of the radiation, resulting in the MNCs becoming over-irradiated during the ECP procedure, leading to the cells prematurely undergoing apoptosis or even necrosis prior to re-entering the patient's bloodstream. In such a case, the intended immune system response may be compromised and may undermine the therapeutic effects of the ECP procedure.

Upon the addition of a photoactivation agent in step 34 of FIG. 5, the MNCs may be irradiated (step 36) and returned to the patient. Alternatively, the MNCs may be returned to the separation component 10, as shown in step 38, where the MNCs may be concentrated (step 40) and supernatant (including unbound photoactivation agent) is separated from the concentrated and treated cells and diverted (step 41). The concentrated cells may be resuspended in a suitable resuspension medium (e.g., plasma, saline) as shown in step 43 and returned to the patient. Prior to returning to the patient, the concentrated and treated cells may be combined with a suitable wash solution (step 42). Where the concentrated cells are combined with wash solution (as per step 42), the MNCs may be again separated from remaining supernatant (step 44). The concentrated and washed MNCs may be resuspended with a resuspension solution (e.g., plasma or saline) as shown in step 45, and returned back to the patient, as shown in step 46.

In one embodiment of MNC collection for conducting an ECP procedure, a target hematocrit of the suspended MNCs may be in the range of 1 to 5%, where hematocrit is determined by the percentage (ratio) of the red blood cells by (per) volume within the suspended MNC product. In another embodiment, the target hematocrit of the suspended MNCs may be in the range of 1.5 to 3%. In yet another embodiment, the target hematocrit of the suspended MNCs may be approximately 2%. A microprocessor-based controller in cooperation with the valves, pumps, weight scales and sensors of device 10 and fluid circuit 200 may be configured to adjust the volume of blood processed in each cycle, according to the number of cycles selected by an operator, to achieve the target hematocrit of the suspended MNCs.

Patient whole blood may be separated by the centrifugal field into a target cell population (e.g., MNCs), an RBC constituent, and a platelet/plasma constituent. In one embodiment, separation and collection of MNCs may proceed in two cycles, as selected by an operator, during which components such as RBCs, plasma, and platelets may be diverted to another container, e.g., container 66 or 67 in FIG. 4, for further processing. Platelets may also be returned to the donor/patient. Collected MNCs may be transferred to container 68 for subsequent irradiation and may contain a small volume of RBCs and plasma/platelets, which may influence the hematocrit of the suspended MNCs.

The first cycle of MNC collection/harvest may be a "full" cycle, in which approximately 2000 mL of whole blood may be processed. During the first cycle, most of the separated RBCs may be directed to container 67, although a small amount of approximately 0.1 to 5 mL of RBCs and approximately 10 mL of plasma may follow the MNCs into the product container 68. The volume of MNCs collected in the first cycle may be approximately 4 to 6 mL. The second cycle of MNC collection may be a "mini" cycle, in which approximately 40 to 60 mL of whole blood is processed. The second cycle may push any remaining MNCs (~2-3 mL) left over from the first cycle in the separation chamber 12, cassettes 23L, 23M, 23R, and/or tubing of the circuit 200, to the product container 68. During the second cycle, any remaining RBCs (~0.1 to 5 mL) in the circuit 200 may also be directed into product container 68 along with the MNCs and approximately 10 mL of plasma. Both cycles may therefore contribute some volume of RBCs to the final collected MNCs within product container 68 to achieve the target hematocrit required for irradiation.

Figure 6:
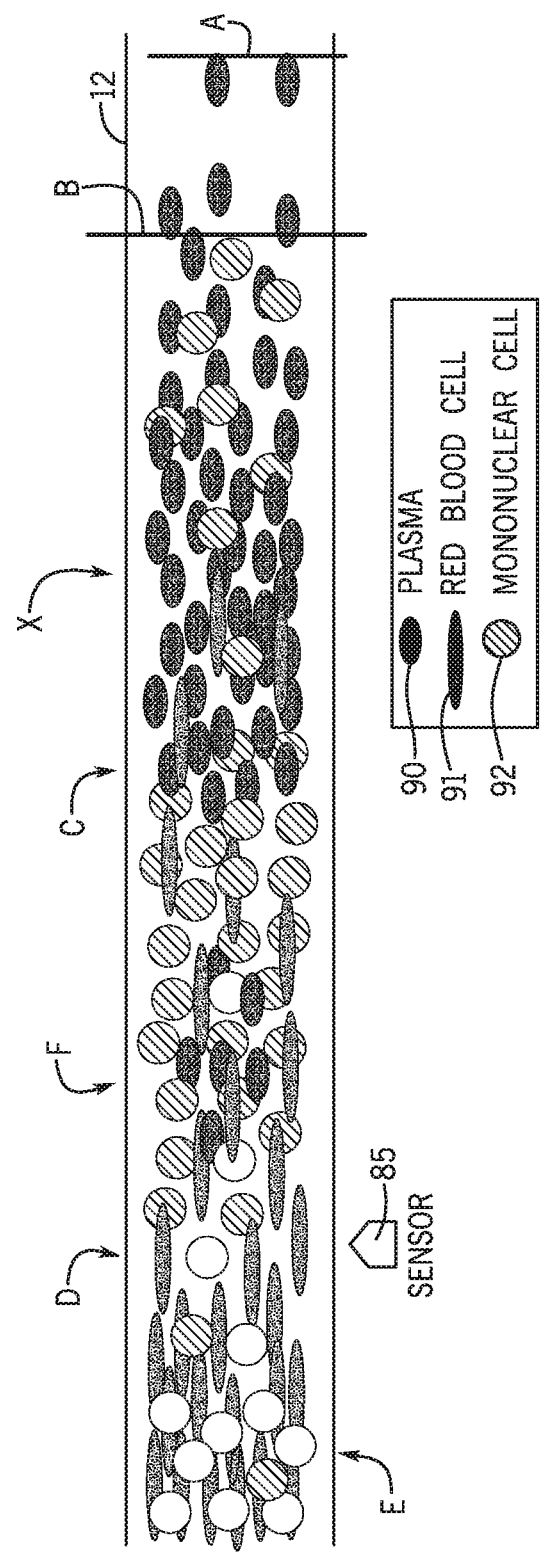
FIG. 6 is a schematic depiction of a longitudinal partial cross section of a fluid flow path as separated blood components flow during an MNC collection and harvest/transfer phase of a cycle, according to an exemplary embodiment.

FIG. 6 is a schematic depiction of a longitudinal partial cross section of a fluid flow path and an optical or hematocrit sensor positioned proximate to the fluid flow path as separated blood components flow (e.g., from left to right in FIG. 6) during an MNC collection and harvest/transfer phase of a cycle, according to an exemplary embodiment. In one embodiment, the sensor may be disposed downstream of the separation chamber 12 at an outlet flow path subsequent to separation, although the sensor may be positioned at any suitable location. FIG. 6 illustrates one mechanism by which the microprocessor-based controller may direct fluid flow into respective containers 66, 67, and 68 (shown in FIG. 4) and thereby influence the hematocrit and relative amounts of plasma, RBCs, and MNCs that end up in the product container 68. For example, the microprocessor-based controller ay cooperate with and receive input from an optical or hematocrit sensor 85 proximate to the separation chamber 12 and direct the various valves, pumps, and clamps of the device to control fluid flow through the fluid circuit according to input it receives regarding light transmission. The optical or hematocrit sensor 85 may be any suitable sensor capable of discerning changes in light transmission reflecting changes in optical density of a liquid. In one embodiment, the optical or hematocrit sensor may comprise one or more diodes emitting one or more wavelengths of light across a fluid flow path towards a diode detector that transduces sensed light into voltage signals capable of being analyzed by a processing unit to compute optical transmission. Examples of optical or hematocrit sensors are described in further detail in U.S. Pat. No. 5,958,250 and the above-mentioned U.S. Pat. Nos. 6,027,657 and 7,282,154, which are incorporated by reference herein in their entireties, although any suitable sensor may be used.

Referring to FIG. 6, point A, according to an exemplary embodiment, marks the beginning of a plasma constituent comprising primarily of plasma 90. At point A, in the case of an optical sensor, the sensor 85 may detect a first designated light transmission level (plasma baseline level), which is a relatively high transmission level, as plasma is relatively more transparent to light than RBCs and MNCs. The baseline plasma transmission level for each procedure may vary among different patients and may be obtained from the patient earlier in the procedure and saved by the controller as the baseline plasma transmission level for that procedure. Point B, according to an exemplary embodiment, marks a point during MNC harvest at which the optical sensor 85 detects an initial phase of the MNCs 92 exiting the separation chamber, which may be an event triggered by the optical sensor detecting a second designated light transmission level. In one embodiment, the second designated light transmission level may be a value approximately 45% less than the first designated light transmission level. Most of the separated MNCs may be concentrated at an interface between the red blood cell constituent and the plasma constituent. At point B, the second designated light transmission level (e.g., approximately 45% lower than the first designated transmission level) may trigger the microprocessor-based controller to prepare for MNC harvest into container 68 (FIG. 4), Based on, for example, a fluid volume distance between the optical sensor 85 and a valve configured to open and direct fluid into container 68 (e.g., valve within cassette 23R in FIG. 4), the controller may be configured to wait for a predetermined or selected volume of fluid to pass the optical sensor 85 prior to opening the valve leading to container 68. The predetermined wait volume may be described as the MNC offset volume, which in one embodiment, may be set to approximately 1.5 mL. The predetermined wait volume may also be set to a time period, for example, the time it takes for the MNC offset volume to flow past the sensor 85. Point C is the end of the MNC offset volume and marks the point at which the controller begins to direct fluid into container 68. Point X, which is a third designated light transmission level approximately 85% lower than the first designated transmission level, marks the point at which the optical sensor 85 detects the first of the RBCs. Following point X, point D marks the point at which the controller stops fluid flow into container 68. As is the case with the MNC offset volume between points B and C, the fluid volume distance between points X and D may be predetermined. The volume distance between points X and D may be characterized as the RBC offset volume. The volume between points C and D is the resulting product volume that is received by product container 68 and is the volume of fluid flowing during the time between the opening and closing of the valve leading to container 68. The volume between points C and D may be characterized as the transferred or harvested volume, which, in one embodiment, is approximately 3 to 10 mL, and may more specifically be approximately 5 to 6 mL.

In an embodiment in which the sensor 85 is a hematocrit sensor, the valve leading to container 68 may be configured to be open from the beginning of the MNC harvest cycle without detecting points A or B. The location of point D may be determined by sensor data in lieu of configuring a predetermined volume distance between points C and D. For example, point X may fall at a point at which the hematocrit sensor 85 detects a threshold hematocrit level, after which a fixed volume is directed to container 68 in order to achieve a target RBC volume per cycle. Preferably, the hematocrit sensor may continuously detect hematocrit values and integrate the values over time to end at point D, at which a known volume of RBCs (RBC volume per cycle) has been directed to container 68.

In certain instances, such as when venous access to a patient is lost, the patient exhibits adverse reactions, for pediatric procedures with lower blood volumes, etc., an operator may choose to shorten the MNC collection procedure and/or decrease the volume of whole blood processed. The operator may have the option to lower the whole blood volume processed per cycle and/or may choose to skip a cycle, e.g., the second mini cycle. In the event the operator chooses to skip the second cycle, the collected MNCs within the product container 68 may have a lower hematocrit because the product container 68 does not receive the RBCs contributed by the second cycle. In other instances, an operator may want to increase the whole blood processed in an ECP procedure in order to increase the number of collected MNCs to be treated. In such a case, an operator may choose to increase the volume of whole blood processed by increasing the number of MNC collection cycles performed, which may increase the hematocrit of the collected MNCs within container 68 due to the cumulative RBC contribution made by each cycle.

Figure 7:
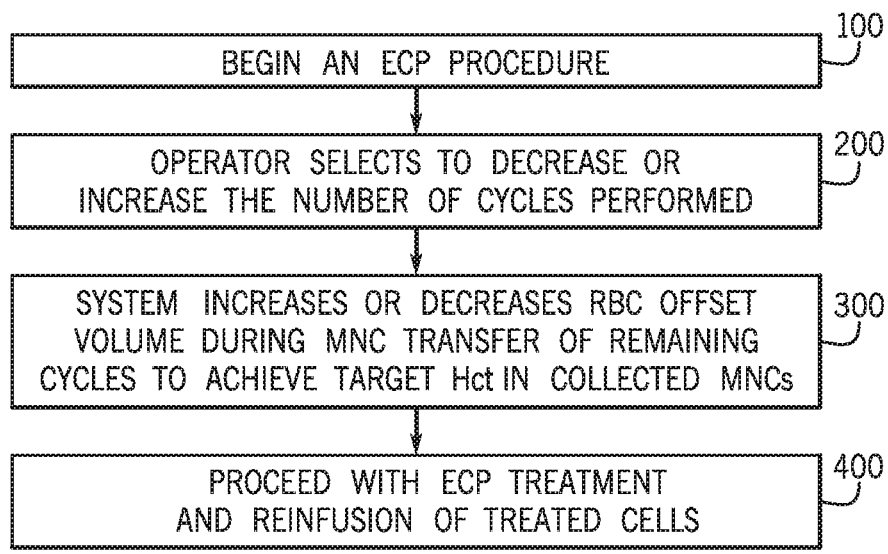
FIG. 7 is a flow diagram illustrating an overview of the steps for increasing or decreasing whole blood volume processed by a photopheresis system, according to an exemplary embodiment.

FIG. 7 shows a flow diagram illustrating an overview of the steps in increasing or decreasing whole blood volume processed by the photopheresis system, according to an exemplary embodiment. Step 100 marks the start of an ECP procedure. At step 200, an operator may set a number of parameters, including a total volume of whole blood to be processed, a number of cycles to be performed, and/or a duration for each cycle. Step 200 may come before or after step 100 depending on preference of the operator and/or the configured settings of component 10 or 20 (FIG. 1). At step 300, based on the parameters set in step 200, the microprocessor-based controller may configure the RBC volume per cycle (or RBC offset volume, in the case of an optical sensor) to achieve the target hematocrit of the suspended MNC product to be collected. At step 400, the MNC collection and harvest may proceed with the configured parameters and offset volumes to obtain the target MNC product.

In one embodiment, an operator may choose to shorten the MNC collection procedure and/or decrease the volume of whole blood processed by choosing to skip the second mini cycle. In such a case, the microprocessor-based controller may re-configure the RBC volume per cycle (or RBC offset volume, in the case of an optical sensor) to be greater than it would be in an embodiment in which the mini cycle is performed, so that the amount of RBCs that would have been contributed by the second cycle may instead be collected in the first cycle.

Referring to FIG. 6, the configuration of the RBC offset volume (step 300 of FIG. 7) in an embodiment in which the second mini cycle is not performed will be described. Point A, according to an exemplary embodiment, marks the beginning of the plasma constituent comprising primarily of plasma 90. At point A, in the case of an optical sensor, the sensor 85 may detect a first designated light transmission level (plasma baseline level). As mentioned above, the baseline plasma transmission level for each procedure may vary among different patients and may be obtained from the patient earlier in the procedure and saved by the controller as the baseline plasma transmission level for that procedure. Point B, according to an exemplary embodiment, marks a point during MNC harvest at which the optical sensor 85 detects an initial phase of the MNCs 92 exiting the separation chamber, which may be an event triggered by the sensor detecting a second designated light transmission level. In one embodiment, the second designated light transmission level may be a value approximately 45% less than the first designated light transmission level. At point B, the second designated light transmission level (e.g., approximately 45% lower than the first designated transmission level) may trigger the microprocessor-based controller to prepare for MNC harvest into container 68 (FIG. 4). The controller may be configured to wait for a MNC offset volume, which in one embodiment, may be set to approximately 1.5 mL, prior to opening the valve leading to container 68. The MNC offset volume ends at point C, according to an exemplary embodiment, which is when the controller directs fluid into container 68 by opening the valve leading to container 68. Point X, which is a third designated light transmission level approximately 85% lower than the first designated transmission level, marks the point at which the optical sensor 85 detects the first of the RBCs. Following point X, point D marks the point at which the controller stops fluid flow into container 68. In an embodiment in which the second mini cycle is not performed, the controller may be configured to close the valve leading to container 68 at point E instead of at point D described previously. The volume distance between points X and E may be characterized as the new RBC offset volume and may be preconfigured based on the cycle settings. In an embodiment in which the sensor 85 is a hematocrit sensor, Point X may be a point at which the sensor 85 detects a threshold level of RBCs at a designated hematocrit value, which in one embodiment, may be approximately 40%. The volume of fluid between point X and point E represents the new RBC volume per cycle, which in an embodiment in which the RBC volume per cycle is preset, may be set within the range of 1 to 11 mL.

In an embodiment in which the sensor 85 is a hematocrit sensor, the valve leading to container 68 may be configured to be open from the beginning of the MNC harvest cycle without detecting points A or B. The location of point E may be determined by sensor data in lieu of configuring a predetermined volume distance between points C and E. For example, point X may fall at a point at which the hematocrit sensor 85 detects a threshold hematocrit level, after which a fixed volume is directed to container 68 in order to achieve a target RBC volume per cycle. Preferably, the hematocrit sensor may continuously detect hematocrit values and integrate the values over time to end at point E, at which a known volume of RBCs (RBC volume per cycle) has been directed to container 68.

In another embodiment, an operator may choose to increase the whole blood processed in an ECP procedure in order to increase the number of collected MNCs to be treated, and/or an operator may choose to increase the number of MNC collection cycles performed. In such a case, the microprocessor-based controller may re-configure the RBC offset volume or RBC volume per cycle to be less than it would be in an embodiment in which only one full cycle and one mini cycle is performed, so that the total amount of RBCs needed to achieve the target hematocrit is collected across the increased number of cycles.

Referring again to FIG. 6, the configuration of the RBC offset volume (step 300 of FIG. 7) in an embodiment in which two full cycles and one mini cycle is performed will be described. Point A, according to an exemplary embodiment, marks the beginning of the plasma constituent comprising primarily of plasma 90. At point A, in the case of an optical sensor, the sensor 85 may detect a first designated light transmission level (plasma baseline level). Point B, according to an exemplary embodiment, marks the point at which the optical sensor 85 detects an initial phase of the MNCs 92, which may be an event triggered by the optical sensor detecting a second designated light transmission level. At point B, the second designated light transmission level may trigger the microprocessor-based controller to prepare for MNC harvest into container 68 (FIG. 4). The controller may be configured to wait for the MNC offset volume prior to opening the valve leading to container 68. The MNC offset volume ends at point C, according to an exemplary embodiment, which is when the system directs fluid into container 68 by opening the valve leading to container 68. Point X, which is a third designated light transmission level approximately 85% lower than the first designated transmission level, marks the point at which the optical sensor 85 detects the first of the RBCs. Following point X, point D marks the point at which the controller stops fluid flow into container 68. In an embodiment in which two full cycles and one mini cycle is performed, the controller may be configured to close the valve leading to container 68 at point F instead of at point D of the previously described embodiment in which one full cycle and one mini cycle are performed. The volume distance between points X and F may be characterized as the new RBC offset volume and may be preconfigured based on the cycle settings. In an embodiment in which the sensor 85 is a hematocrit sensor, Point X may be a point at which the hematocrit sensor 85 detects a threshold level of RBCs at a designated hematocrit, e.g., approximately 40%. The volume of fluid between point X and point F represents another reconfigured RBC volume per cycle, which in an embodiment in which the RBC volume per cycle is preset, may be set within the range of 0.5 to 8 mL.

In an embodiment in which the sensor 85 is a hematocrit sensor, the valve leading to container 68 may be configured to be open from the beginning of the MNC harvest cycle without detecting points A or B. The location of point F may be determined by sensor data in lieu of configuring a predetermined volume distance between points C and F. For example, point X may fall at a point at which the hematocrit sensor 85 detects a threshold hematocrit level, after which a fixed volume is directed to container 68 in order to achieve a target RBC volume per cycle. Preferably, the hematocrit sensor may continuously detect hematocrit values and integrate the values over time to end at point F, at which a known volume of RBCs (RBC volume per cycle) has been directed to container 68.

The increase or decrease in the RBC offset volume or RBC volume per cycle may be the same for each cycle or may be variable throughout the procedure. For example, in an embodiment in which at least one full cycle and at least one mini cycle is performed, the RBC offset volume or RBC volume per cycle may be set to different values depending on the type of cycle with consideration made with regard to variable RBC contribution amounts by different types of cycle.

If the number of cycles or type of cycle is adjusted at any point during the procedure, the system may re-determine the RBC offset or RBC volume per cycle for any remaining cycles, taking into account how many cycles have been performed and with what corresponding RBC offsets/volumes. The system may also increase the volume of whole blood processed per cycle in order to reduce the number of remaining cycles while still achieving the target total whole blood volume processed and target hematocrit in the collected MNCs.

In another embodiment in which an operator chooses to shorten the MNC collection procedure, decrease the volume of whole blood processed, and/or the MNC product has a lower hematocrit than the target hematocrit, the microprocessor-based controller may be configured to transfer RBCs directly from the RBC container 67 (FIG. 4) after MNC transfer completes. RBCs may be directed from container 67 to the product container 68 to increase the hematocrit to the target level. For example, in one embodiment in which an operator chooses to perform one full cycle and one mini cycle, the volume of RBCs directed from container 67 to container 68 may be in the range of 2 to 10 mL.

Figure 8:
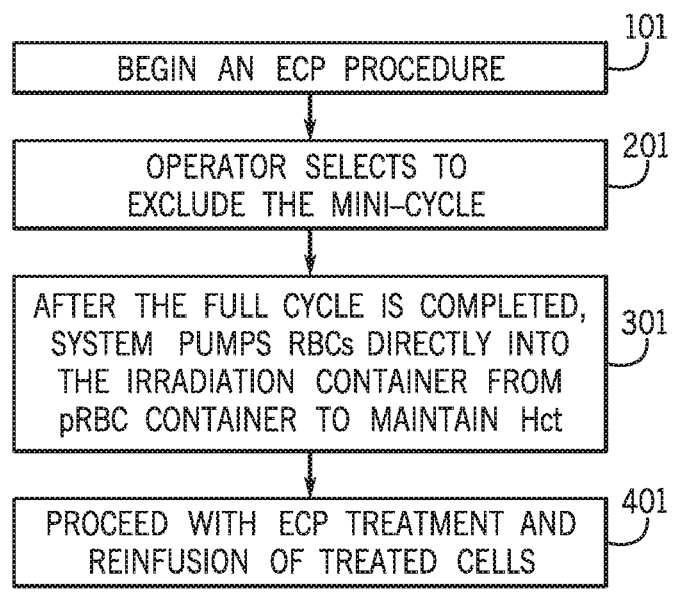
FIG. 8 is a flow diagram illustrating an overview of the steps for increasing hematocrit of the MNC product, according to an exemplary embodiment.

FIG. 8 shows a flow diagram illustrating an overview of the steps in increasing hematocrit of the MNC product, according to an exemplary embodiment. Step 101 marks the start of an ECP procedure. At step 201 an operator may set a number of parameters, including a total volume of whole blood to be processed, a number of cycles to be performed, and/or duration for each cycle. Step 201 may come before or after step 101 depending on preference of the operator. At step 301, based on the parameters set in step 200, the microprocessor-based controller may transfer RBCs directly from the RBC container 67 to the product container 68 (FIG. 4) to achieve the target hematocrit of the suspended MNC product to be collected. It may be desirable for hematocrit to be increased due to, e.g., having performed a fewer number of cycles for MNC harvest than necessary to obtain adequate hematocrit. At step 401, the MNC irradiation and treatment may proceed.

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

The invention claimed is:

1. A system for collecting mononuclear cells to be treated with UV irradiation, comprising: a disposable fluid circuit comprising a processing container, a product container configured to receive a mononuclear cell product comprising mononuclear cells, red blood cells, and plasma, a tubing connecting the processing container to the product container; a separator configured to work in association with the disposable fluid circuit, the separator comprising a chamber configured to receive the processing container, rotate about a rotational axis and convey whole blood into an inlet region of the chamber for separation into a red blood cell constituent, a plasma constituent, and an interface constituent carrying mononuclear cells between the red blood cell constituent and the plasma constituent, a valve for selectively permitting fluid flow through the tubing, an optical or hematocrit sensor configured to detect transmission levels of light passing through separated blood components flowing out of the processing container through the tubing; a microprocessor-based controller in communication with the separator, wherein the controller is programmed to: receive input of a target hematocrit for the mononuclear cell product, wherein hematocrit is determined by a ratio of the red blood cells per volume within the mononuclear cell product; receive input for a total volume of whole blood to be processed and a number of cycles to be performed; direct the interface constituent and a portion of the red blood cell constituent into the product container by opening the valve disposed between the processing container and the product container to collect a resulting mononuclear cell product volume comprising a volume of mononuclear cells and a volume of red blood cells; and automatically adjust the volume of red blood cells flowed to the product container based on input from the optical or hematocrit sensor so that a ratio of total volume of red blood cells within the mononuclear cell product to a total volume of mononuclear cell product equals the target hematocrit.

2. The system of claim 1 wherein the controller is programmed to measure the red blood cell volume from a point at which the optical or hematocrit sensor detects, respectively, a designated light transmission level or designated hematocrit that is, respectively, approximately 85% less than a baseline plasma level or approximately 40% HCT.

3. The system of claim 2, wherein the resulting product volume is in the range of 1 to 11 mL.

4. The system of claim 1, wherein the target hematocrit is in the range of 1 to 5%.

5. The system of claim 1, wherein the target hematocrit is approximately 2%.

6. The system of claim 1, wherein the total volume of whole blood to be processed is approximately 2000 mL.

* * * * *